United States Patent

Wächter et al.

[11] Patent Number: 5,880,370
[45] Date of Patent: *Mar. 9, 1999

[54] TESTING HEAD ARRANGEMENT FOR CORRECTING THE ANGLE OF SOUND ENHANCE USING A CORRECTION SKID

[75] Inventors: Michael Wächter, Ratingen; Kurt Hannoschöck, Sonsbeck; Dieter Grohs, Niederkassel-Mondorf; Peter Steinert, Kerpen; Wolfgang Zydek, Wesseling, all of Germany

[73] Assignee: Krautkrämer GmbH & Co., Wurselen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 515,736

[22] Filed: Aug. 16, 1995

[30] Foreign Application Priority Data

Aug. 16, 1994 [DE] Germany ............... 44 30 604.0

[51] Int. Cl.⁶ .................................................. G01N 29/26
[52] U.S. Cl. ................................................. 73/634; 73/622
[58] Field of Search ........................... 73/634, 635, 637, 73/638, 639, 641, 622, 588, 598, 600

[56] References Cited

U.S. PATENT DOCUMENTS

| 3,504,534 | 4/1970 | Mandula, Jr. | 73/641 |
| 3,512,081 | 5/1970 | Skubiak | 73/634 |
| 4,117,733 | 10/1978 | Gugel | 73/634 |
| 4,255,972 | 3/1981 | Dijkstra | 73/634 |
| 4,526,037 | 7/1985 | Wentzell | 73/634 |
| 4,532,808 | 8/1985 | Wentzell | 73/634 |

Primary Examiner—Christine K. Oda
Attorney, Agent, or Firm—John Lezdey & Assoc

[57] ABSTRACT

In a device for the arrangement of at least one ultrasonic testing head on a tube having a welding seam for the ultrasonic testing of the welding seam of the tube each ultrasonic testing head is built in a support. The support is provided with front and rear support points and led in constant radial distance to the tube on a test trace. The ultrasonic testing head is arranged in the area of the front support points, which are closest to the welding seam to be examined seen in the peripheral direction of the tube. A mechanical scanning device is provided, it is connected to the ultrasonic testing head and is arranged at the support in the area between the front and rear support points. The ultrasonic testing head has a single ultrasonic vibrator.

6 Claims, 5 Drawing Sheets

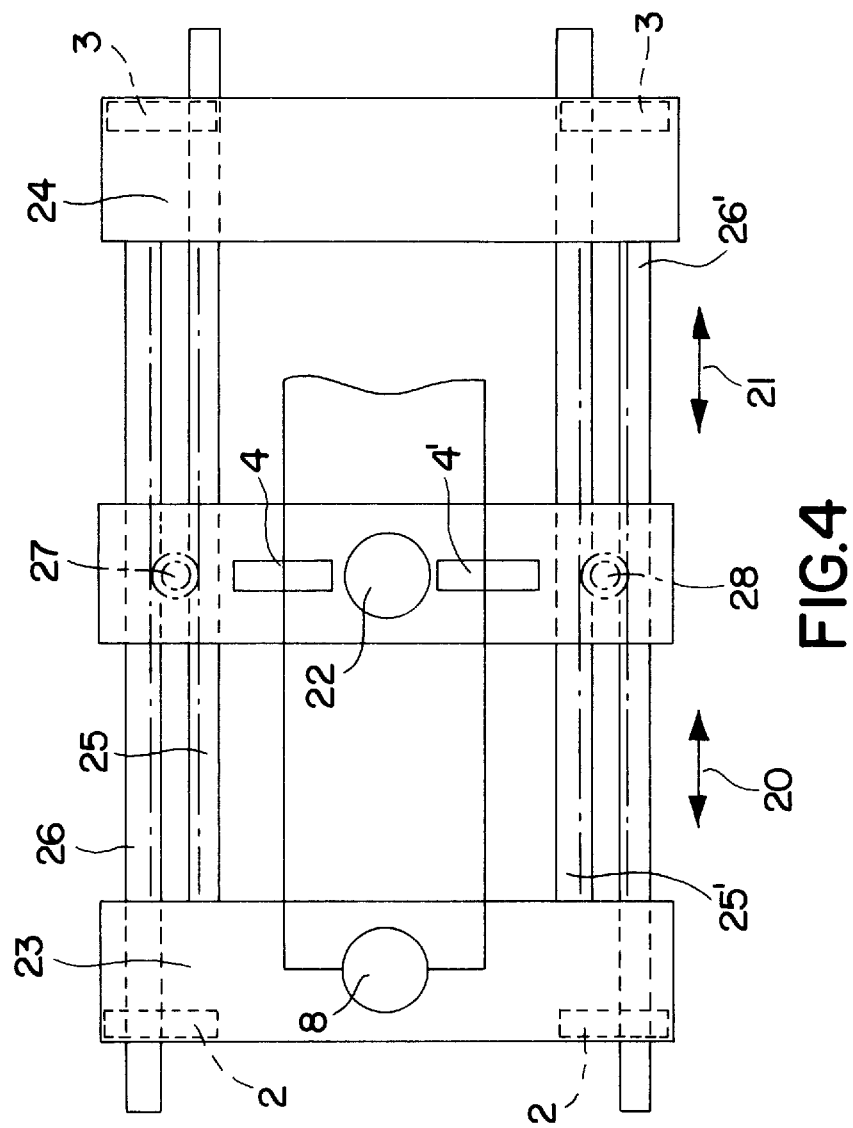

TESTING HEAD ARRANGEMENT FOR CORRECTING THE ANGLE OF SOUND ENHANCE USING A CORRECTION SKID

BACKGROUND OF THE INVENTION

1. Field of the Invention

The invention relates to an arrangement of at least one ultrasound testing head in a test system for the ultrasonic testing of a welding of a tube seam.

2. Description of the Prior Art

When testing the welding seam of tubes for longitudinal errors, especially with tubes having large diameters, it is necessary for some tasks to get as closely as possible to the welding seam. For leading the ultrasound-testing head a support is used, which shows two support-points each on both ends in the peripheral direction. Normally the sound-entrance point is situated with the systems known in the peripheral direction of the tube centric between the support points of the locating arrangement. This has the advantage that the angle of sound entrance once chosen stays the same for all diameters of the tube and the optimal angle of sound entrance can be measured at a device with a plane supporting surface. With this arrangement the possible minimal distance welding seam edge/sound-entrance point is half of the distance of the support points of the locating arrangement.

If the test task requires to get closer to the welding seam edge with the sound-entrance point, the distance of the support points would have to be maximized so much with a locating arrangement and with a centric sound-entrance point, that the front support point seen from the peripheral direction of the tube lies on one side of the welding seam, while the rear support point and the sound entrance point lies on the opposite point of the welding seam. Disadvantages of this arrangement are:

a) The distance of the support points of the locating arrangement needs to be changed to different distances for the sound-entrance point to the welding seam edge, meaning, in some cases, that no indicator optimization by continuous change of skip distance is possible.

b) Seam edge racking can sometimes occur (meaning, different sheet metal heights on both seam sides) which can lead to undefined changes of the angle of the sound-entrance point.

c) In the arrangement described earlier, a belt control with the help of the passing-sound is not possible.

SUMMARY OF THE INVENTION

The disadvantages described earlier can be solved in such a way that the sound-entrance point is shifted from the middle of the locating arrangement to the front support point. This is also called the acentric sound-entrance point. With this arrangement it is possible to enter the sound directly next to the welding seam edge and there is no hindrance with the indicator-optimization. For different tube diameters, however, one has to always adjust the angle of sound-entrance. Also, the angle of sound-entrance on the measuring device with a plane supporting surface cannot be controlled any longer.

It is the task of the invention to develop a device to improve the known locating arrangements for at least one ultrasound testing head in a test system for the ultrasonic testing of the welding seam of a tube, with which the angle of sound-entrance is possible on a plane surface with the acentric sound-entrance point and no adjustment of the angle of sound-entrance is required for different diameters of tubes.

This problem is solved by the present invention as disclosed hereinafter and in the characterizing portion of claim 1. Advantageous developments are disclosed in the dependent claims.

According to the invention a mechanical scanning device connected to the test head is arranged in the area between the front and rear support points. The test head has a single ultrasonic vibrator. The test head arranged between the front support points acts as an individual oscillator. Depending on the diameter of the tube the scanning device according to the invention is pressed in to different depths. Referring to FIG. 1 and the following formulae, the line segment x, which the scanning device grasps, has to be transferred for large diameters of tubes in the relation 1:2 to the angle correction. The line segment x is also referred to as a reference value for the correction of the angle, which measures the curvature of a tube to be tested. For flat surfaces, this reference value is zero.

The abbreviations used in FIG. 1 have the following meanings:

R=radius of the circular cross-section of the tube to be examined

M=center of the circular cross-section

Alpha=angle between the sides (M-scanning device and M-front support point)

x=way of the scanning device (reference point for the angle correction)

x'=distance of the scanning device to the closed tangent situated at the front support point $$R/(R+x')=\cos\ alpha=(R-x) \tag{1}$$

$$R2=(R-x)(R+x')=R2+Rx'-Rx-xx' \tag{2}$$

$$Rx=x'(R-x) \tag{3}$$

$$x'=Rx/(R-x) \tag{4}$$

for big R relative to x, x equals x'

The centric scanning enables an automatic correction of the angle of sound-entrance caused by the radius of the pipe bend with a sound-entrance at the front support point.

The advantages of the proposed arrangement can be seen in the fact that with the impulse reflection test the place of sound—entrance can be chosen continually changeable in any distance to the welding seam edge starting with 0. The angle of sound—entrance once set is valid for all diameters of a tube.

With the tandem test it is also possible to sound-in directly next to the welding seam. The testing heads function as a transmitter and a receiver. The sending and receiving testing heads can be arranged closely next to each other. The testing heads will be angularly corrected automatically according to the diameter of the tube. Other aspects, objects and advantages of the invention will more fully appreciated with reference to the drawings and the following description of the preferred embodiments.

BRIEF DESCRIPTION OF THE DRAWINGS

FIG. 4 is a top view of a practical embodiment of the variant according to FIGS. 3a, 3b.

DESCRIPTION OF THE PREFERRED EMBODIMENTS

Figure 1:
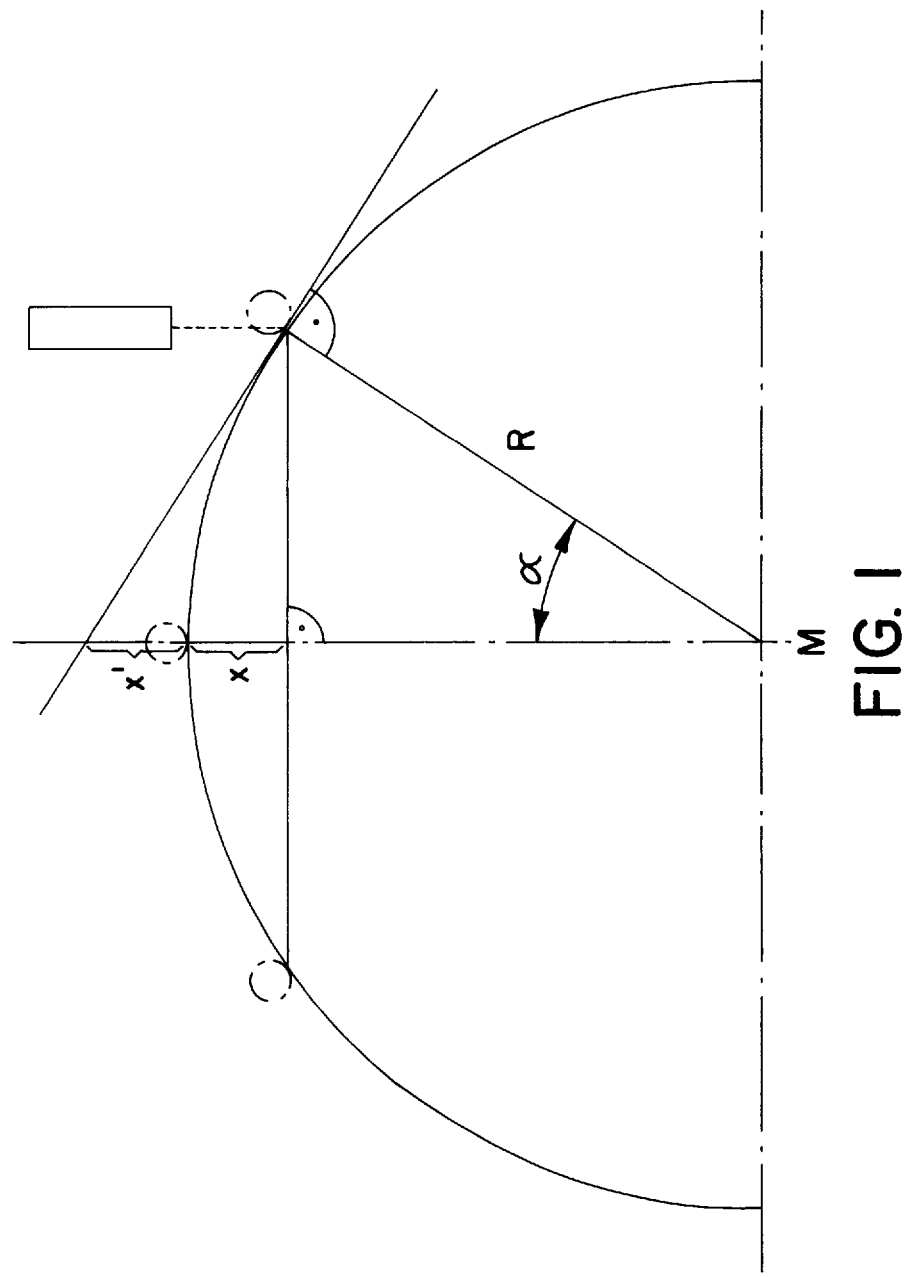
FIG. 1 is a schematic illustration of an arrangement with a scanning device and front support points and the angles and paths taken therein which illustrate the abbreviations used in formulae (1)–(4) hereinafter.

FIG. 1 illustrates the scanning device and front support points. Also shown in FIG. 1 are the path of the scanning device, the radius of the circular cross-section of the tube to be examined, the center of the circular cross-section of the tube to be examined, the center of the circular cross-section and the angle between the sides. Measurements are made through the formulae disclosed in the Summary of the Invention.

Figure 2A:
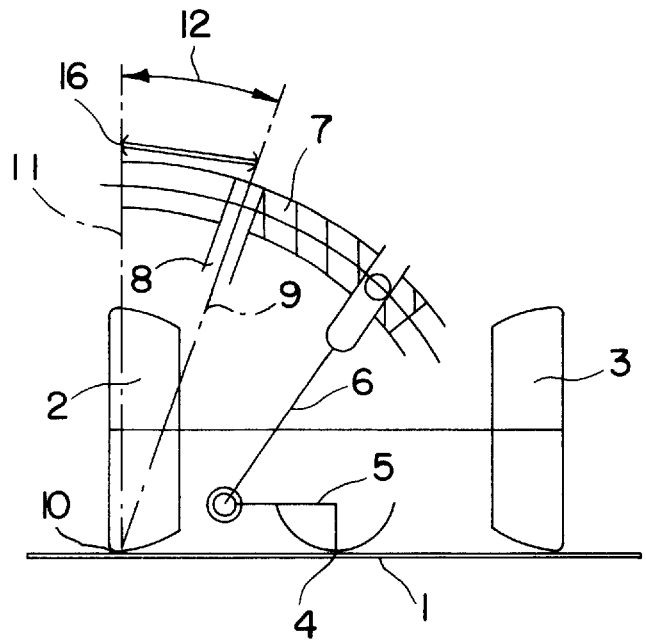
FIG. 2a is a schematic illustration of an arrangement with a testing head and a base angle adjustment setting on a plane surface.
Figure 2B:
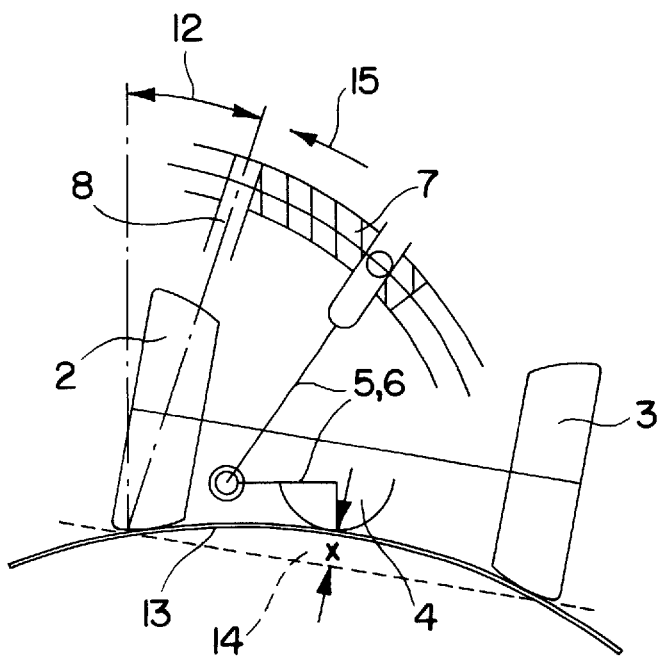
FIG. 2b as 2a, but correction of the angle on the bend surface.

In the FIGS. 2a and 2b a first embodiment of the device according to the invention is illustrated in a schematic illustration. The base angle adjustment takes place via an adjusting piece 16 on a plane surface 1. The support for the testing heads shows two support points, which are projected preferably as carbide wheels 2, 3, carbide skids or harden rolls. The mechanical scanning device automatically angularly corrects the testing heads. The scanning device is connected to the test head and mounted on the support in an area between the front and rear support points in a form of a correction skid. The test head has a single ultrasonic vibrator and acts as an individual oscillator when it is arranged between the front support points. The scanning device according to the invention between the two support points 2, 3 is projected as correction skid 4. This correction skid 4 is prolonged by a transformation lever system 5, 6, connected to a link 7. On the link 7 the testing head 8 is secured as roughly indicated in the drawings. The prolongation of the sound beam axis 9 up to the plane surface 1 equals the sound-entrance point 10. Between sounding line 11 and sound beam axis 9 is the angle of incidence 12. If according to the illustration in FIG. 2b the support for the testing head is put on a bend surface, then according to the invention a correction of the angle occurs automatically via the moving correction skid 4. As can be seen clearly from FIGS. 2a and 2b, the skid is pressed in deeper using the line segment x, also illustrated as reference numeral 14, as the reference value for the correction of the angle. Via the lever system 5, 6 a shifting of the link 7 in the direction of the arrow 15 occurs. The testing head 8 connected to the link 7 is then also shifted so that the angle of incidence alpha 12 originally set on the plane surface 1 (FIG. 2a) stays the same.

Figure 3A:
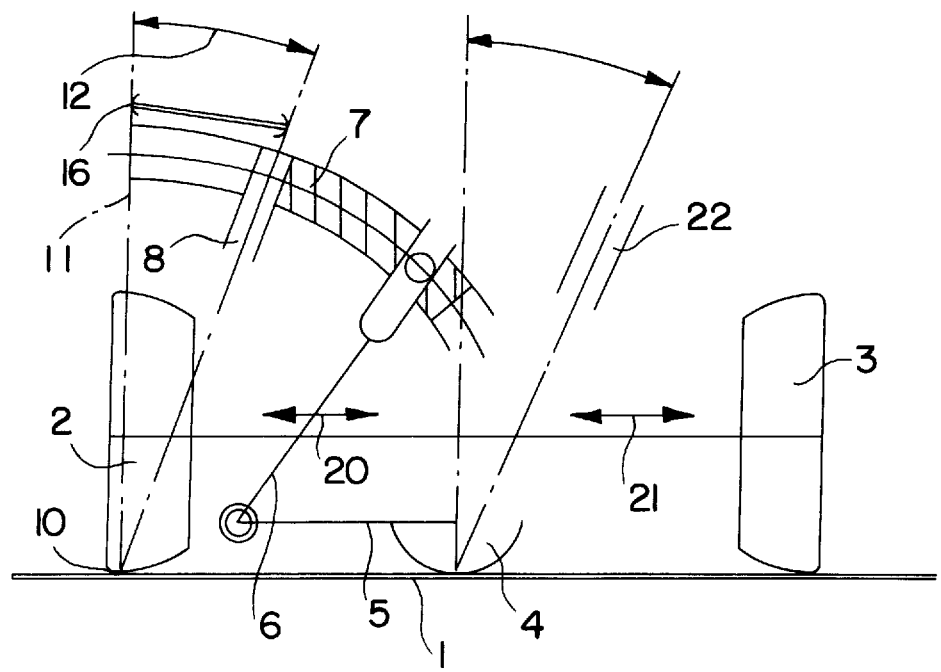
FIG. 3a as 2a, but with 2 testing heads in a support.
Figure 3B:
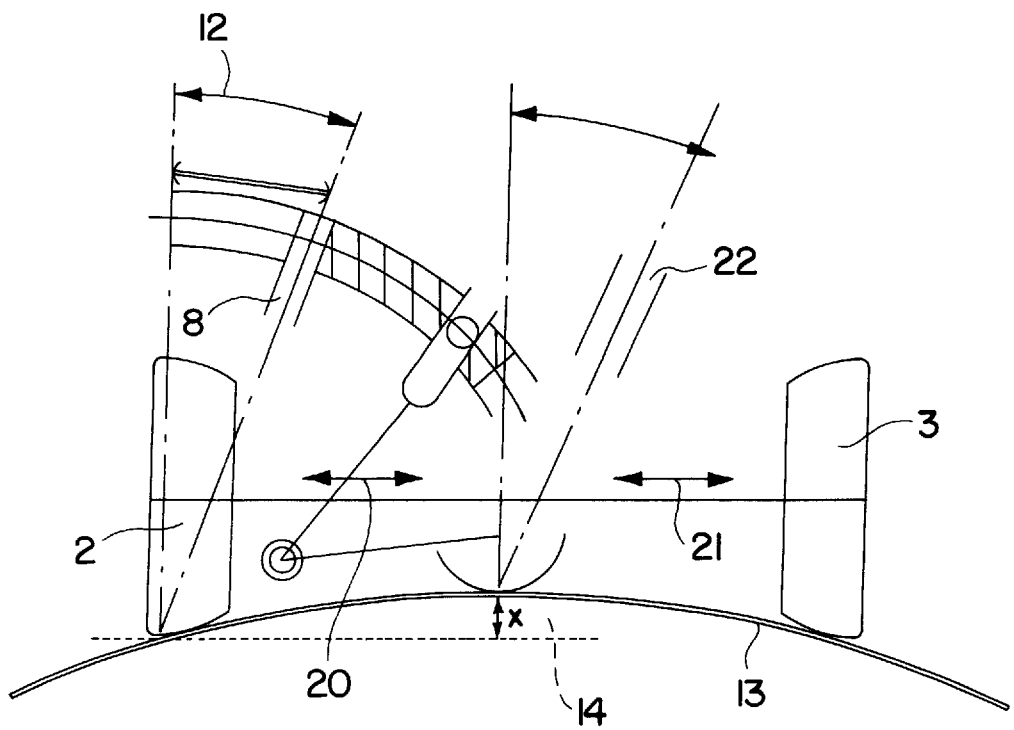
FIG. 3b as 2b, but with two testing heads in a support.

In the FIGS. 3a, 3b, a further embodiment is shown using the same reference numerals as used in FIGS. 2a, 2b. In this embodiment two testing heads 8, 22 are arranged in one support. The changing of the distance for the testing heads occurs via a symmetrical shifting of the support heads 2, 3 to the center. It is marked by two arrows 20, 21. The first testing head 8 is connected mechanically per the link 7 and the lever system 5, 6 with the correction skid 4 as the one in FIGS. 2a, 2b. The correction of the angle after having put on the support for the testing head on a bend surface 13 occurs in the same way as described earlier. For the second testing head 22 no correction is necessary, as the centric setting between the support points 2, 3 is ensured by the symmetrical movement of the support points 2, 3. The advantage of this tandem arrangement can be seen in fact that the two testing heads 8, 22 can be arranged next to each other by keeping the angle correction according to the invention.

FIG. 4 shows a top view of a practical embodiment of the variant according to FIGS. 3a, 3b. The support for the testing head consists of two sheet metal holders 23, 24, which are connected to each other by two countercurrent toothed racks 25, 25'; 26, 26', spindles or the like. A gear wheel 27, 28 is situated between each of the two racks 25, 26, both arranged at a distance. The correcting skids 4, 4' for the correction of the angle of the first testing head 8 are only indicated here. The lever system as well as the links were omitted for the sake of simplicity. This arrangement ensures that with changes of the distance between the two testing heads 8, 22 according to the arrows 20, 21, the centric arrangement of the second testing head 22 between the two support points 2, 3 is kept constant.

Figure 5:
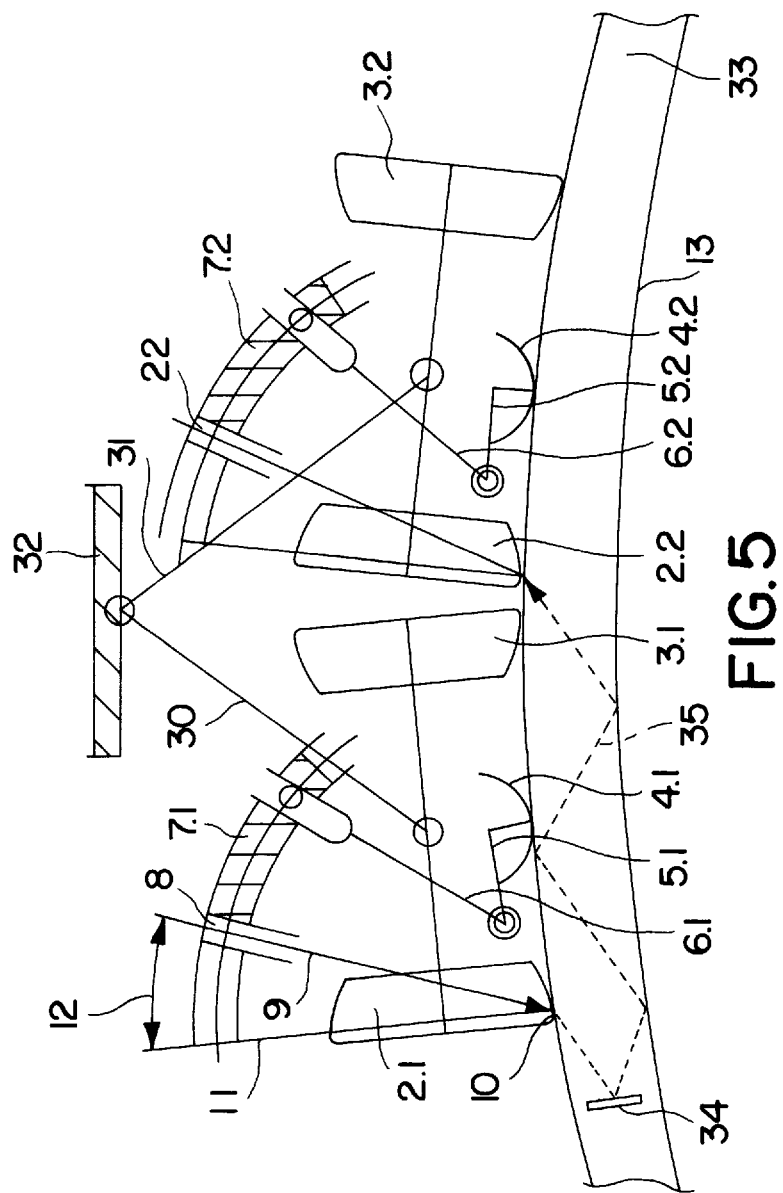
FIG. 5 is a schematic illustration of an arrangement with 2 supports for testing heads with Cardanic connection in separated correction skids.

In an illustration comparable to FIG. 2b, FIG. 5 shows a further embodiment with two separate supports for testing heads with Cardanic connection and separate correction skids, where the same reference numerals were used for the same parts common to both figures. In comparison to the illustrations of FIGS. 3a, 3b and FIG. 4, the second testing head 22 in FIG. 5 is also secured to a link 7.2 so that it can also be corrected in the angle. The linking of the two supports for the testing heads occurs via a Cardanic lever system 30, 31, 32. The cardanic connection connects the second support to the first support. The bend surface 13 is symbolized here by a partial cross-section of a tube 33. As an illustration, an exaggerated mistake 34 is drawn onto the wall. This mistake 34 is hit by the sound beam 9 of the first testing head 8, reflected (dotted line marking line 35) several times in the wall and received in the second testing head 22.

What is claimed is:

1. An improved device for the ultrasonic testing of a weld seam on a metal tube, said device having at least one ultrasonic testing head directed onto the tube at an angle of sound-entrance, each of said at least one ultrasonic testing head being built in a support having front and rear support points in a constant radial distance to the tube on a test trace, wherein the testing head is arranged in the vicinity of the front support points which are closest to the weld seam to be tested as seen in the peripheral direction of the tube, the improvement comprising a mechanical scanning device for correcting the angle of sound-entrance of the at least one testing head measured from a plane surface, the scanning device being connected to the at least one ultrasonic testing head and mounted on the support in an area between the front and rear support points in a form of a correction skid and a transformation lever system, the transformation lever system being arranged between the correction skid and the at least one testing head so that movement of the correction skid causes movement of the at least one testing head, the correction skid being arranged in a distance from the at least one testing head so as to cause a variation in the prolongation of a sound beam axis up to the plane surface, and the at least one testing head comprising a single ultrasonic vibrator.

2. A device according to claim 1, wherein said scanning device is arranged centric between the front and rear support points.

3. A device according to claim 1, further comprising at least a second ultrasonic testing head, wherein said support comprises a plurality of parts having shifting means which symmetrically shift the first and second testing heads which are arranged so that the second testing head is situated further from the welding seam while remaining centric between the front and rear support points.

4. A device according to claim 1, wherein the front and rear support points comprise a material selected from the group consisting of carbide skids and hardened rolls.

5. An improved device for the ultrasonic testing of a weld seam on a metal tube, said device having at least a first and a second ultrasonic testing head directed onto the tube at an angle of sound-entrance, each of said ultrasonic testing heads being built in a first and second support, each of said supports having front and rear support points in a constant radial distance to the tube on a test trace, wherein each of said testing heads is arranged in the vicinity of the front support points which are closest to the weld seam to be tested as seen in the peripheral direction of the tube, the improvement comprising a mechanical scanning device for correcting the angle of sound-entrance of each of said testing heads, the scanning device being connected to the ultrasonic testing head and mounted on each of said respective support in an area between the front and rear support points in a form of a correction skid, and each of said testing heads comprising a single ultrasonic vibrator and a second support, the second support being connected via a Cardanic connection with the first support, said first and second supports having a scanning device for correcting the angle of the respective testing heads.

6. A device according to claim 5, wherein the first testing head of the first support comprises a transmitter and the second testing head of the second support comprises a receiver.

\* \* \* \* \*